(12) United States Patent
McNair

(10) Patent No.: US 11,869,671 B1
(45) Date of Patent: Jan. 9, 2024

(54) CONTEXT-SENSITIVE HEALTH OUTCOME SURVEILLANCE AND SIGNAL DETECTION

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 49 days.

(21) Appl. No.: 15/671,939

(22) Filed: Aug. 8, 2017

Related U.S. Application Data

(63) Continuation of application No. 13/616,235, filed on Sep. 14, 2012, now abandoned.

(60) Provisional application No. 61/534,729, filed on Sep. 14, 2011.

(51) Int. Cl.
    *G16H 50/70* (2018.01)
    *G16H 10/60* (2018.01)

(52) U.S. Cl.
    CPC ............ *G16H 50/70* (2018.01); *G16H 10/60* (2018.01)

(58) Field of Classification Search
    CPC .. G06Q 40/08; G06Q 10/10; G06Q 50/22–24; C12Q 1/6886; G06F 19/324; G06N 5/04
    See application file for complete search history.

(56) References Cited

U.S. PATENT DOCUMENTS

| | | | |
|---|---|---|---|
| 6,000,828 A | * | 12/1999 | Leet ....................... G16H 70/60 705/2 |
| 6,778,994 B2 | | 8/2004 | Gogolak |
| 7,418,478 B1 | | 8/2008 | Orling et al. |
| 7,461,006 B2 | | 12/2008 | Gogolak |

(Continued)

OTHER PUBLICATIONS

Soden, Sarah E et al., "Effectiveness of exome and genome sequencing guided by acuity of illness for diagnosis of neurodevelopmental disorders", Published Dec. 3, 2014, Sci. Trans !. Med. vol. 6, Issue 265, 14 pages. Available at: http://stm.sciencemag.org/content/6/265/265ra168.full.html.

(Continued)

*Primary Examiner* — Robert W Morgan
*Assistant Examiner* — Edward B Winston, III
(74) *Attorney, Agent, or Firm* — Kilpatrick Townsend & Stockton LLP

(57) ABSTRACT

Systems, methods and computer-readable media are provided for facilitating patient health care through automatic discovery, establishment, and statistical validation of safety signals in repositories of EMR information, identifying safety signals regarding therapeutics or therapeutics combinations administered to patients. In an embodiment, a method includes identifying, from a dataset of health care records, a first group of patients that received a drug; extracting one or more medical events that the first group experienced; identifying a second group of patients similar to the first group who have received one or more concomitant comparator drugs that address the same set of conditions that prevail in both the first group and second group; extracting one or more medical events that the second group of patients have experienced; and comparing the medical events of the first group to the medical events of the second group to determine statistically significant differences in occurrences between the groups.

20 Claims, 9 Drawing Sheets

(56) References Cited

U.S. PATENT DOCUMENTS

| | | |
|---|---|---|
| 7,650,262 B2 | 1/2010 | Pearson et al. |
| 7,856,362 B2 | 12/2010 | Walker |
| 7,917,374 B2 | 3/2011 | Walker |
| 7,966,196 B2 | 6/2011 | Walker |
| 7,979,373 B2 | 7/2011 | Gogolak |
| 10,431,336 B1 | 10/2019 | Murrish et al. |
| 11,380,440 B1 | 7/2022 | McNair |
| 2002/0165852 A1* | 11/2002 | Gogolak ............... G06N 5/04 |
| 2005/0050077 A1* | 3/2005 | Li ...................... G06F 16/2465 |
| 2006/0111847 A1* | 5/2006 | Pearson ............... G16H 70/60 |
| | | 702/19 |
| 2006/0235727 A1* | 10/2006 | Singer .................. G06Q 10/00 |
| | | 705/2 |
| 2007/0294113 A1 | 12/2007 | Settimi |
| 2008/0091471 A1* | 4/2008 | Michon ................ G16B 40/20 |
| | | 705/3 |
| 2008/0215402 A1* | 9/2008 | Pearson ............ G06Q 30/0204 |
| | | 705/7.33 |
| 2008/0228043 A1 | 9/2008 | Kenedy et al. |
| 2008/0233574 A1 | 9/2008 | Castonguay et al. |
| 2008/0305962 A1* | 12/2008 | Wirtz .................. C12Q 1/6886 |
| | | 506/9 |
| 2009/0055378 A1 | 2/2009 | Alecu et al. |
| 2009/0299645 A1 | 12/2009 | Colby et al. |
| 2009/0326985 A1* | 12/2009 | Martin .................. G16H 15/00 |
| | | 705/2 |
| 2010/0169108 A1* | 7/2010 | Karkanias ............ G16H 50/20 |
| | | 705/2 |
| 2011/0104062 A1* | 5/2011 | Siu ................... G01N 33/57407 |
| | | 435/7.1 |
| 2013/0185096 A1 | 7/2013 | Giusti et al. |
| 2013/0231404 A1 | 9/2013 | Segal |
| 2013/0238359 A1 | 9/2013 | Carter et al. |
| 2014/0222349 A1 | 8/2014 | Higgins et al. |
| 2014/0342919 A1 | 11/2014 | Seddon |
| 2014/0379379 A1 | 12/2014 | Janevski et al. |
| 2015/0017636 A1 | 1/2015 | Prichard et al. |
| 2015/0073719 A1 | 3/2015 | Glynias et al. |
| 2015/0088870 A1 | 3/2015 | Jayasundera et al. |
| 2015/0205690 A1 | 7/2015 | Seto |

OTHER PUBLICATIONS

Boden, Sarah E et al., Supplementary Materials for "Effectiveness of exome and genome sequencing guided by acuity of illness for diagnosis of neurodevelopmental disorders", Published Dec. 3, 2014, Sci. Trans!. Med vol. 6, Issue 265, 14 pages. Available at: http://stm.sciencemag.org/content/suppl/2014/12/01/6.265.265ra168.DC1.html.

Non-Final Office Action received for U.S. Appl. No. 15/008,439, dated Jun. 6, 2019, 19 pages.

Non-Final Office Action received for U.S. Appl. No. 15/008,439, dated Aug. 18, 2020, 39 pages.

Final Office Action received for U.S. Appl. No. 15/008,439, dated Oct. 3, 2019, 29 pages.

U.S. Appl. No. 13/616,235, Final Office Action dated Feb. 9, 2017, 19 pages.

U.S. Appl. No. 13/616,235, Final Office Action dated Jul. 30, 2015, 20 pages.

U.S. Appl. No. 13/616,235, First Action Interview Office Action Summary dated Oct. 8, 2014, 20 pages.

U.S. Appl. No. 13/616,235, First Action Interview Pilot Program Pre-Interview Communication dated Apr. 24, 2014, 5 pages.

U.S. Appl. No. 13/616,235, Non-Final Office Action dated Jun. 17, 2016, 18 pages.

U.S. Appl. No. 15/008,439, Non-Final Office Action dated Sep. 20, 2021, 12 pages.

U.S. Appl. No. 15/008,439, Non-Final Office Action dated Aug. 18, 2020, 39 pages.

U.S. Appl. No. 15/008,439, Notice of Allowance dated Feb. 18, 2022, 8 pages.

Final Office Action received for U.S. Appl. No. 15/008,439, dated Feb. 22, 2021, 11 pages.

\* cited by examiner $$P(q|x) = P(q) \frac{P(x_1|q)}{P(x_1)} \frac{P(x_2|q)}{P(x_2)} \cdots \frac{P(x_n|q)}{P(x_n)}$$

FIG. 4A.

| MEDICATION OR COMBO OR CONCOMITANT MEDS | RECEIVED MED OR COMBO (% OF TOTAL) | ACTUAL NBR DIED (% RCVD) | EXPECTED NBR DIED | RELATIVE RISK | ACT/EXP | P-VALUE** | NNH |
|---|---|---|---|---|---|---|---|
| CIPROFLOXACIN | 386 (5.8%) | 129 (33.4%) | 28.3 | 5.9 | 4.6 | < 0.0001 | 3.1 |
| AMIODARONE +PHENYTOIN | 39 (0.6%) | 13 (33.3%) | 3.7 | 5.9 | 3.5 | < 0.0002 | 3.6 |
| IBUPROFEN +AZITHROMYCIN | 25 (0.4%) | 7 (28.0%) | 2.2 | 4.9 | 3.1 | < 0.01 | 4.5 |
| IBUPROFEN +CIPROFLOXACIN | 24 (0.4%) | 6 (25.0%) | 2.5 | 4.4 | 2.4 | < 0.05 | 5.2 |
| VALPROIC ACID | 53 (0.8%) | 12 (22.6%) | 4.8 | 4.0 | 2.5 | < 0.004 | 5.8 |
| AMIODARONE +LEVOFLOXACIN | 277 (4.1%) | 49 (17.7%) | 26.5 | 3.1 | 1.8 | < 0.0001 | 8.0 |
| ACETAMINOPHEN +PHENYTOIN | 135 (2.0%) | 24 (17.8%) | 8.5 | 3.1 | 2.8 | < 0.0001 | 8.1 |
| PHENYTOIN | 158 (2.4%) | 27 (17.1%) | 9.7 | 3.0 | 2.8 | < 0.0001 | 8.6 |
| AMIODARONE +AZITHROMYCIN | 65 (1.0%) | 9 (13.8%) | 4.6 | 2.4 | 1.9 | < 0.05 | 12.1 |
| ACETAMINOPHEN +AZITHROMYCIN | 277 (4.1%) | 31 (11.2%) | 18.0 | 2.0 | 1.7 | < 0.003 | 17.4 |
| LEVOFLOXACIN | 736 (11.0%) | 79 (10.7%) | 51.4 | 1.9 | 1.5 | < 0.0001 | 17.6 |
| AZITHROMYCIN | 327 (4.9%) | 33 (10.1%) | 20.8 | 1.8 | 1.6 | < 0.006 | 21.5 |
| ONDANSETRON +CIPROFLOXACIN | 245 (3.7%) | 24 (9.8%) | 16.6 | 1.7 | 1.4 | < 0.0001 | 23.4 |
| FLUOXETINE | 131 (2.0%) | 11 (8.4%) | 4.9 | 1.5 | 2.2 | < 0.02 | 36.0 |
| ENTIRE COHORT | 6,699 (100%) | 380* (5.7%) | N/A | 1.0 | N/A | N/A | N/A |

| MEDICATION OR COMBO OR CONCOMITANT MEDS | RECEIVED MED OR COMBO (% OF TOTAL) | ACTUAL NBR GR.4 LIVER INJ (% RCVD) | EXPECTED NBR GR. 4 LIVER INJ | RELATIVE RISK | ACT/EXP | P-VALUE | NNH |
|---|---|---|---|---|---|---|---|
| IBUPROFEN +LEVOFLOXACIN | 58 (0.9%) | 9 (15.5%) | 3.5 | 5.3 | 2.5 | < 0.02 | 7.8 |
| AMIODARONE +LEVOFLOXACIN | 277 (4.1%) | 35 (12.6%) | 18.1 | 4.3 | 1.9 | < 0.0003 | 9.8 |
| AMIODARONE +IBUPROFEN | 110 (1.6%) | 12 (10.9%) | 5.8 | 3.8 | 2.1 | < 0.02 | 12.2 |
| LEVOFLOXACIN | 736 (11.0%) | 54 (7.3%) | 35.7 | 2.5 | 1.5 | < 0.001 | 19.9 |
| ONDANSETRON +LEVOFLOXACIN | 439 (6.6%) | 32 (7.3%) | 20.4 | 2.5 | 1.6 | < 0.01 | 21.1 |
| VENLAFAXINE | 111 (1.7%) | 8 (7.2%) | 3.6 | 2.5 | 2.2 | < 0.04 | 22.7 |
| ENTIRE COHORT | 6,699 (100%) | 192 (2.9%) | N/A | 1.0 | N/A | N/A | N/A |

FIG. 4B.

| | Drug(s) | Nbr Received Med or Combo | Exposure Prev. | AE1 (In-House Mort) | | AE2 (Gr-1) | AE3 (Gr-2) | AE4 (Gr-3) | AE5 (Gr-4) | Hep Tox % |
|---|---|---|---|---|---|---|---|---|---|---|
| 1 | acetaminophen | 5120 | 76.4% | 263 | 5.1% | 1798 | 818 | 526 | 147 | 2.9% |
| 2 | allopurinol | 149 | 2.2% | 6 | 4.0% | 57 | 21 | 11 | 7 | 4.7% |
| 3 | amiodarone | 1496 | 22.3% | 129 | 8.6% | 599 | 338 | 253 | 70 | 4.7% |
| 4 | amlodipine | 893 | 13.3% | 44 | 4.9% | 297 | 111 | 64 | 18 | 2.0% |
| 5 | atorvastatin | 2391 | 35.7% | 81 | 3.4% | 822 | 389 | 258 | 48 | 2.0% |
| 6 | azithromycin | 327 | 4.9% | 33 | 10.1% | 159 | 71 | 44 | 17 | 5.2% |
| 7 | captopril | 168 | 2.5% | 8 | 4.8% | 71 | 41 | 33 | 10 | 6.0% |
| 8 | carbamazepine | 27 | 0.4% | 2 | 7.4% | 10 | 4 | 2 | 1 | 3.7% |
| 9 | chlorpromazine | 41 | 0.6% | 2 | 4.9% | 17 | 15 | 5 | 2 | 4.9% |
| 10 | ciprofloxacin | 386 | 5.8% | 52 | 13.5% | 203 | 92 | 69 | 26 | 6.7% |

EXAMPLE POPULATION: AMI IN-PATIENTS BETWEEN 35 AND 60 YEARS OLD (ADM IN 2008-2010 WITH LOS > 3D AND LFTS > 0)
TOTAL POPULATION = 6699
TOTAL NUMBER DIED = 380 (5.7%)
NUMBER WITH GRADE-4 LIVER FAILURE = 192 (2.9%)

*FIG. 5A.* TO 5B. ➡

CONTEXT-SENSITIVE HEALTH OUTCOME SURVEILLANCE AND SIGNAL DETECTION

CROSS REFERENCE TO RELATED APPLICATIONS

This application is a continuation application of U.S. patent application Ser. No. 13/616,235 filed on Sep. 14, 2012, which claims the benefit of U.S. Provisional Application No. 61/534,729, titled "Context-Sensitive Health Outcome Surveillance And Signal Detection," filed Sep. 14, 2011, both of which are hereby expressly incorporated by reference in their entirety.

INTRODUCTION

The safety of medications, medical devices, and therapeutic procedures is a matter of great concern worldwide, both to public health agencies and regulators and to health care providers, insurers, and consumers. It is a matter of great economic importance to manufacturers of therapeutic products, insofar as their financial success and sustainability depends on making sure that their products have acceptable safety and do not become the subject of tort litigation or regulator-mandated removal from the market. Increasingly, the safety of therapeutic products is evaluated not only in pivotal clinical trials that form the basis for regulatory approval and market launch, but also in post-market surveillance observational studies. Such studies include registries and Phase IV "open" clinical trials, but also traditionally include statistical analysis of spontaneous adverse event reports that are received by regulatory agencies.

The U.S. Adverse Event Reporting System (AERS) contains over 3 million adverse event reports spontaneously submitted by health care providers, pharmaceutical companies, and the public since 1968. The World Health Organization's Vigibase system likewise contains millions of spontaneous adverse event reports. For coding adverse events, these systems currently utilize the CIOMS Medical Dictionary for Regulatory Activities (MedDRA) classification system with over 15,000 preferred terms (PTs). AERS currently has about 10,000 PTs and 4,000 generic drug names in use. Thus, approximately 43 million drug-event combinations (DECs) are possible in the AERS database.

However, considered as a two-way (drug-by-event) table, the AERS database is quite sparsely populated. Only approximately 2.8 million (0.7%) of approximately 43 million possible DECs have ever been spontaneously reported by humans. A large proportion (67%) of the 2.8 million DECs that have been reported one or more times contain fewer than three reports, and approximately half of the DECs exist only once. The sparseness of spontaneous reports in the AERS and Vigibase and similar databases may arise predominantly from the considerable limitations of human pattern recognition and logistical and sociological factors that inhibit people from preparing and submitting spontaneous adverse event reports. In other words, the sparseness of spontaneous reports is not necessarily evidence of the absence of safety issues for drug-event combinations that have never received spontaneous reports. And, in fact, the sparseness and the skewed frequency distributions of spontaneous reports cause significant limitations in the ability of systems that rely on spontaneous reports to detect safety signals in a sensitive, specific, and timely manner—even for the drug-event combinations that have received some spontaneous report activity.

In this connection, data mining is a potentially useful adjunct to traditional pharmacovigilance methods. The results of data mining should be viewed as an empirical means of signal-detection and hypothesis-generating and should be evaluated in the context of other relevant data. Empirical Bayes (EB) and Multi-item Gamma Poisson Shrinker (MGPS) and the Proportional Reporting Ratio (PRR) methods can be used to classify adverse events as signals based on the disproportionality of these events in databases and to prioritize the pursuit of other relevant data to assess causality and potential remedies to mitigate safety issues that are detected and validated.

Conventionally, aggregate analysis of observational data consists of examining differences in outcome frequency between a group having the exposure of interest, and groups lacking that exposure. But the groups must be similar at 'baseline'. If they are not, then interpretation will have a high rate of false-positive and false-negative errors. The International Society for Pharmacoepidemiology (ISPE) in its 2004 commentary on FDA Guidance documents specifically cautions against calculating PRR reporting rates using the entire safety database to derive an expected rate, asserting that a more appropriate expected rate is the PRR for comparable chemical entities with similar indications, or at least all drugs with comparable indications to reduce the number of false-positive signals due to the disease being treated or its known and expected complications.

Traditionally, however, signal detection in pharmacovigilance operations does not obey this principle but instead entails pooling all medication exposures and all adverse event types (AEs). However, the patient populations receiving different medication regimens are vastly different with different statistical distributions of diagnoses, disease severity levels, and physiologic reserve (ability to tolerate physiologic stresses and recover from them, with transient abnormalities during the period of challenge reverting to normal after the challenge is removed). The consequence is that pooling all populations and all AE types leads to excessive false-negative rates of signal detection.

Rather than "all exposures—all AEs," it would be preferable instead to perform safety signal detection by comparing drug-AE incidence rates in a manner that considers "context-sensitive exposures context-relevant AEs." For example, morphine, acetaminophen, aspirin, atorvastatin, lisinopril, metoprolol, and ondansetron are empirically prescribed in more than 35% of all AMI in-patients and may be considered to be part of contemporary de facto standard of care.

For patients facing serious or life-threatening illness, the goals and objectives of care generally do not permit abating curative or salvific interventions, or eliminating medications that are essential to saving the patient's life, and so forth, even if those curative interventions confer substantial risk of AEs or serious side-effects. The calculus of rational therapy decisions involves balancing benefits against risks. Situations where the risk of acute mortality is 30% or greater can justify utilizing therapeutic options that themselves may carry up to 30% likelihood of serious harm.

The current state of knowledge about unsafe combinations of therapeutic interventions is limited by the finite ability of human beings to notice and understand complex multivariable patterns of information, especially causative patterns or chains of events that unfold over a period of time or ones that transcend the customary scope of responsibility and authority that a particular person has. Pairwise drug-drug interaction databases reflect the ability of humans to notice and report adverse outcomes that arise when two things in combination are associated with one event type that is proximate in time to the exposure to that combination. However, patterns of interactions that involve three or more drugs or combinations of one or more drugs concomitantly with multiple patient attributes or one or more antecedent therapeutic procedures are well beyond the abilities of average humans to notice or comprehend. Consequently, safety issues with such multivariable patterns presently remain undetected, and guidances warning against them are never published. Embodiments of the invention provide systems and methods for detecting such characteristic patterns and safety signals; establishing them in defined, context-specific populations where their meaning and statistical significance can be reliably interpreted; and tracking the incidence and evolving statistical strength of the safety signals over time.

SUMMARY

Systems, methods and computer-readable media are provided for facilitating patient health care through the automatic discovery, establishment, and statistical validation of safety signals in repositories of electronic medical record (EMR) information, identifying safety signals regarding new or existing therapeutics or combinations or sequences of therapeutics administered to patients, either in an acute or chronic health care setting or in an ambulatory/home setting. For example, in one embodiment, a database of health care claims is utilized and the method includes identifying from the database a first group of patients that have received a drug; extracting one or more medical events that the first group of patients have experienced; identifying a second group of patients who are similar to and matched on attributes of the first group and who have received one or more concomitant comparator drugs that address the same set of conditions that prevail in both the first group and second group; extracting one or more medical events that the second group of patients have experienced; and comparing the one or more medical events of the first group to the one or more medical events of the second group to determine one or more statistically significant differences in occurrences between the groups. In embodiments, the method further includes computing a probability value for each of the one or more common safety event type occurrences. In this way, embodiments of the invention may be used to identify and quantify the probability that certain medical events will occur to patients exposed to the drug, or combination of drugs, or combination of drugs, comorbid conditions, and concomitant therapeutic interventional procedures or devices.

BRIEF DESCRIPTION OF THE DRAWINGS

Embodiments of the invention are described in detail below with reference to the attached drawing figures, wherein:

FIG. 4A provides example results from an embodiment of our invention, sometimes referred to herein as Event Surveillance System or DiscernESS™, showing detection of statistically significant medication combinations that were associated with increased relative risk of in-hospital patient death;

FIG. 4B provides example results of an embodiment showing detection of statistically significant medication combinations that were associated with increased relative risk of developing in-hospital, life-threatening Grade 4 drug-associated liver injury.

FIGS. 5A and 5B illustratively show a portion of results from the application of the embodiment described above in connection to FIGS. 4A and 4B.

DETAILED DESCRIPTION

Figures 1A, 1B:
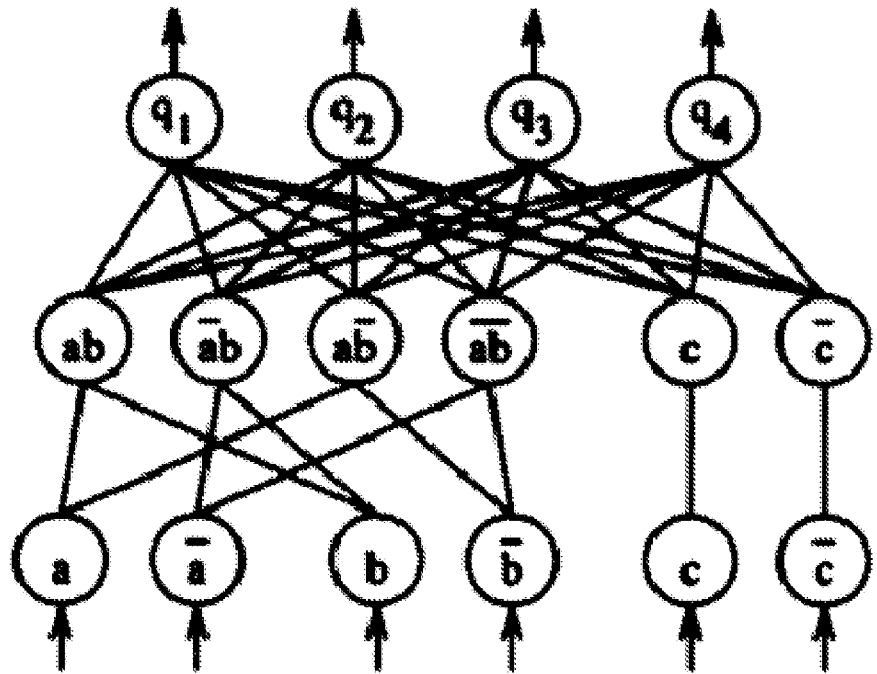
FIG. 1A illustrates an example Bayesian confidence-propagation neural network having one 'complex' or 'compound' column variable (ab) and one simple first-order column variable (c)
FIG. 1B provides an equation of Bayes theorem for the probability of $q_j$ conditioned on x where there is one unit for each outcome of each input variable given as xi (where i is 1 to n) and one unit for each output class qj.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

A technology is provided for facilitating patient health care through the automatic discovery, establishment, and statistical validation of safety signals in repositories of electronic medical record (EMR) information, identifying safety signals regarding new or existing therapeutics or combinations or sequences of therapeutics administered to patients, either in an acute or chronic health care setting or in an ambulatory/home setting.

Empirically Balancing Likely Benefits and Risks Under Uncertainty

Generally, it is not sensible to embark on a therapeutic option where the population-level 'number-needed-to-treat' (NNT) or the individually personalized NNT for the therapeutic benefit substantially exceeds the 'number-needed-to-harm' (NNH) for an AE type that occurs with a substantial frequency (i.e., NNT1/NNH2>1.0). In terms of principles of evidence-based medicine, the metrics 'number-needed-to-treat' (NNT) and 'number-needed-to-harm' (NNH) are used to assess the balance of probable benefits and harms.

But the 'exposure-negative' row in the 2×2 contingency tables that are used to compute NNT and NNH should contain counts for an alternative intervention that has adequate efficacy for treating the same condition as the counts for the agent in the 'exposure-positive' row reflect. Contrary customary practice, the 'exposure-negative' row should not be filled with counts for cases whose treatment regimen does not address the condition.

An NNT is treatment-specific and describes the difference between a treatment and a control in achieving a particular desirable clinical outcome, such as survival. Similarly, an NNH is treatment-specific and describes the difference between a treatment and a control in causing a particular undesirable clinical outcome, such as liver injury or mortality. It can be used to describe any outcome where event rates are available for both a treatment and a control.

Bayesian confidence-propagation neural network (BCPNN) algorithms are one means by which probabilities for various beneficial events and harmful events or outcome states can be jointly computed from multiple concurrent input variables, where the variables' values may be time-dependent or uncertain.

With reference to FIGS. 1A and 1B, Bayesian confidence-propagation neural networks are designed to calculate the probabilities of some output attributes (classes) from the values of input variables by a computational abstraction involving one or more interconnected "layers." If there is one unit for each outcome of each input variable xi and one unit for each output class qj, the Bayes theorem provides the equation, shown in FIG. 1B, for the probability of $q_j$ conditioned on x.

With further reference to FIG. 1B, ordinarily, the computation involves taking the logarithm, in which case the right-hand side becomes a discrete sum. Each term corresponds to the coefficient (weight) associated with input variable $x_i$ to the output class qj. Each output class unit sums its inputs and exponentiates the result, yielding the desired probability. In the network shown in FIG. 1A, there is one 'complex' or 'compound' column variable (ab) and one simple first-order column variable (c).

One of the goals of spontaneous reporting systems is to protect the public health by providing an early warning system for previously unknown serious adverse drug reactions (ADRs). A driving principle of these systems is the suspicion of possible causal relationships between AEs and drugs, which prompts the reporter to submit a spontaneous report. In the course of investigating these reports, drug safety personnel may receive information on events, adverse or otherwise, that occurred after the drug was administered, but were not the intended subject of the spontaneous report. These events which did not prompt contact with the pharmaceutical company or regulator and for which there is no evidence of drug causality are usually defined as 'incidental events' by the Council for International Organizations of Medical Sciences (CIOMS) V Working Group. However, the "absence of evidence" of causality does not constitute "evidence of absence" per se. It frequently happens that an evidence of a safety signal or a causal relationship simply has not been noticed or reported by humans.

Data analysis methods that have been used with spontaneous report data include the Multi-Item Gamma Poisson Shrinker (MGPS), the Proportional Reporting Ratio (PRR) method, and the Bayesian Confidence Propagation Neural Network (BCPNN). However, none of these methods has previously been supported with a system and method that (1) automatically insures that the exposed and non-exposed groups have comparable attributes and clinical needs that must be addressed therapeutically with some drug or intervention or combination of drugs or interventions, nor are the prior art methods capable of (2) adaptively and automatically examining interactions beyond first-order "drug-event" pairs.

Embodiments of the invention are directed to reliably detecting safety signals that include not only first-order but also second- and higher-order combinations and sequences of therapeutics that are associated with adverse events or undesirable outcomes. Some embodiments utilize BCPNN, MGPS, and PRR to multi-laterally ascertain statistically significant increases or decreases in the relative risk of specific outcomes that are associated with various therapeutic interventions (such as specific medications or combinations of medications or specific doses or cumulative exposures to a medication or combination; or invasive procedures such as surgeries; or plans of care or treatment protocols) in the context of the population attributes and severity of illness attributes that are of interest. Some embodiments match sub-cohorts based on attribute vectors of diagnoses and correlate these with the approved clinical on-label indications for various medications. This matching forms the basis for assembling appropriate aggregates of exposed and non-exposed subjects, so that false-positive and false-negative error rates of signal detection are substantially reduced compared to prior art systems. Control of false-positive error is performed using an FDR algorithm, such as that of Benjamini and Hochberg, in a manner similar to FDR usage in genomic microarray data analysis.

Embodiments of the invention address the problem of safety signal detection and validation and tracking, primarily as part of an observational program of vigilance following regulatory approval of a therapeutic health product, such as a drug or a biologic or a medical device, or of an interventional procedure or service. Other methods that are conventionally used for the evaluation of drug safety signals (including major signals leading to withdrawal of products from the market) are inconsistent and sometimes of poor quality. While the assessment of the safety of medicines and other therapeutics needs to consider specific issues such as drug interactions and variation in compliance, the general principles, which are used to study environmental hazards, can be applied for this purpose. The criteria proposed more than 35 years ago by Austin Bradford-Hill for attributing disease or health outcome causation to environmental factors have been used widely in epidemiology, are today widely applied to pharmacovigilance and pharmacoepidemiology. The Austin Bradford-Hill criteria include strength and consistency of evidence; statistical specificity; temporality of the adverse event to exposure to its putative cause(s); biological gradient associated with increased incidence of the adverse event; causal plausibility; and logical and mechanistic coherence.

But these other methods have several limitations:

(1) To detect a safety signal, human beings, who have finite attention spans and finite scope of responsibility and authority with regard to performing surveillance and comprehending the various exposures and outcomes that arise for any one patient or for a population of patients in their care, must perceive patterns of multiple antecedent variables and multiple events and outcomes that may potentially be caused by or consequent upon these patterns, thereby constituting an unexpected occurrence relating to safety. Upon noticing such a pattern occurrence, they must further take the initiative to electively document the event and pattern and manually submit a spontaneous adverse drug report (ADR) or an adverse event report to the relevant regulatory or public health agency. The fact that these acts take time, for which the submitters receive no compensation, leads to significant under-reporting and a dearth of submissions. Furthermore, the fact that, in many cases, the humans perceive substantial medical malpractice or other risk that would be incurred were they to undertake to report an event or pattern that they have witnessed contributes to substantial under-reporting of adverse events.

(2) Frequently, humans fail to notice relevant patterns. Often, this is because the patterns involve multiple variables that collectively constitute the pattern or criteria that define the event. Sometimes it is because the multiple variables include some that are beyond the scope of any particular individual's responsibility to observe or understand. The person who orders one test or panel of tests may not be responsible for monitoring the results of tests that are ordered by other persons or that are ordered at different times in the course of care. As a result of this fragmentation of responsibility and oversight, safety signals that involve multi-variable patterns are distinctly unlikely to be detected or spontaneously reported by anyone involved in the care process.

(3) The psychology of physicians and other providers who care for patients facing serious and life-threatening conditions is such that they are less likely to spontaneously report adverse events involving therapeutics that were prescribed in an attempt to save the patients' lives. In such contexts, the nature of the therapeutic doctor-patient relationship is such as to be biased against spontaneous reporting, insofar as the mortality and other risks that are inherent in the context are already large and clinicians have difficulty ascertaining whether a serious adverse event that does occur is 'incidental', or would have occurred anyway, or whether by contrast it is an event that may be causally related to the therapy chosen and constitutes an unreasonable balance of marginal risks that are not outweighed by major benefits of the therapeutic choice. It is far easier to discern rare and unexpected serious adverse events and causal relationships among relatively "well" ambulatory patients. As a result, there are significant under-recognition and under-reporting of adverse events and product safety issues in acute-care hospital populations, in long-term care and nursing home populations, and in other populations that have relatively high morbidity and severity-of-illness.

(4) Some important adverse reactions or safety event types arise with such low frequency that, although serious or life-threatening, it is improbable that any one practitioner would encounter even one of them during a lifetime of practice. As such, even the practitioner who does encounter one or two occurrences is often disposed to regard the events as 'incidental' or random. In the absence of strong financial or other incentives to think deeply about the occurrence and attempt to understand it or report it, the natural tendency is to dismiss it without reporting it and proceed on to the care of other patients.

(5) Episode-oriented case-level and longitudinal patient-level information are neglected, often omitted from regulatory agencies' spontaneous reporting forms. Instead, only event-level information is captured. This 'collocation', event-scoped regime inadvertently and powerfully dis-incentivizes the recognition of concomitant and longitudinal exposures that transgress the boundaries of the index episode in which the current event or case arises, with consequent false-negative errors (failure do detect true safety signals).

(6) Some data mining techniques utilize processing methods that result in substantial delays in signal detection, compared to conventional spontaneous adverse report safety analyses.

(7) What is happening in practice is that drug manufacturers must report AEs and ADRs in such a way that they are indistinguishable from each other in the spontaneous reporting databases. In addition, seriousness is recorded on reporting forms and electronic file formats at the "case" level and not at the "event" level. This results in an inability to discriminate serious from nonserious adverse events. Both of these issues result in excessive false-negative (Type II) involving serious adverse events and false-positive (Type I) errors involving nonserious and/or incidental adverse events, which impairs the ability of reviewers to detect true serious safety signals and protect the public health.

(8) Some data mining techniques depend either on (a) absolute uniformity in nomenclature, which tends to limit the size and diversity of systems that are able to contribute to the data warehouse for data mining and signal detection, or they depend on (b) loose textual or semantic matching, which is valuable for some case-finding (positives) but often is unable to accurately ascertain exposures and nonexposures and is likewise often unable to accurately rule-out or ascertain nonoccurrences (negatives). Consequently, automatic inter-systems ontology mapping services are important in order to achieve repositories having adequate sample size and diversity such that interpretations are not statistically confounded by unmeasured factors that are associated with the use of any particular vendor's EMR or other source system recording the exposures and events that materialize subsequent to the exposures.

(9) Alternative prior art solutions that require detailed construction of database retrieval extracts where the extracted cohorts embody homogeneous populations give rise to labor-intensive activities requiring individuals of high levels of expertise. As a result, such systems are too expensive to operate on a comprehensive or sustainable basis.

(10) Prior art methods are not able to accommodate the very large proliferation of event-types that would occur if events were stratified according to their severity or according to their duration or reversibility. But if there is a physiologic mechanism whereby an agent causes an outcome, one naturally expects to find a quantitative dose-response relationship in the data, where increasing quantitative exposures are associated with more frequent, severe, longer-lasting, or irreversible outcomes. The binomial analysis limitation of prior art methods results in significant false-negative errors. An important capability to detect causal relationships from quantal strata is foregone.

(11) Prior art systems are in general unable to discern differences among different strengths or mg/kg dosages or particular dosage-forms or routes of administration or, for medical devices, are unable to discern differences among various versions or models or sizes or peri-procedural constellations of collateral treatments or other factors. Instead, they are only able to do case-finding and analysis upon coarse, binomial "exposed"/"not-exposed" status.

(12) While some EMR-based methods have recently appeared, these do not properly balance the comparator population against the attributes of the candidate population for adverse event discovery and ascertainment.

(13) Prior art solutions that are based on administrative transactions, prescriptions, orders, claims, and other episode-scoped information often lack detailed date-time stamped information denoting the minute-wise timing of when medication-administration exposures occurred and when any events materialized. As such, all such systems are able to ascertain is simple statistical 'association', not causality. By contrast, some modern EMR systems capture such detailed exposure and laboratory test result and clinical event information for each item with minute-wise precision. Additionally, some such EMR systems record the excursions that frequently happen when physicians modify patients' orders over time—involving exposure (therapeutic "challenge") for a period of time; dose-range adjustment of the dose or concomitant medications over a subsequent period of time; discontinuation of therapy ("de-challenge") in yet a subsequent period of time, for one reason or another; and re-prescribing of the drug again over a period of time ("re-challenge"). These EMR systems capture these time stamped exposure excursions together with the date-time stamped succession of event occurrences such as materialize during these excursions. From such challenge-dechallenge-rechallenge excursions it is possible to deduce causal relationships. However, prior art systems fail to take advantage of this naturally-occurring data in modern EMR systems or data warehouse repositories derived from them.

(14) Conventional prior art methods emitting safety signals often leads to regulatory removal of the product from the market, when in fact no safer effective alternative exists. In other words, such systems are logically similar to "placebo-controlled" clinical trials that imply that "not treating" the condition is a viable, rational, ethical option, which is not true. It is neither rational nor ethical in a majority of instances. Therefore, instead the comparator group for safety signal detection should preferably be restricted to individuals who are receiving some sort of treatment ("active control") for the condition of interest.

Accordingly, it would be valuable and highly desirable to provide a novel approach for mitigating the aforementioned limitations.

Figure 2A:
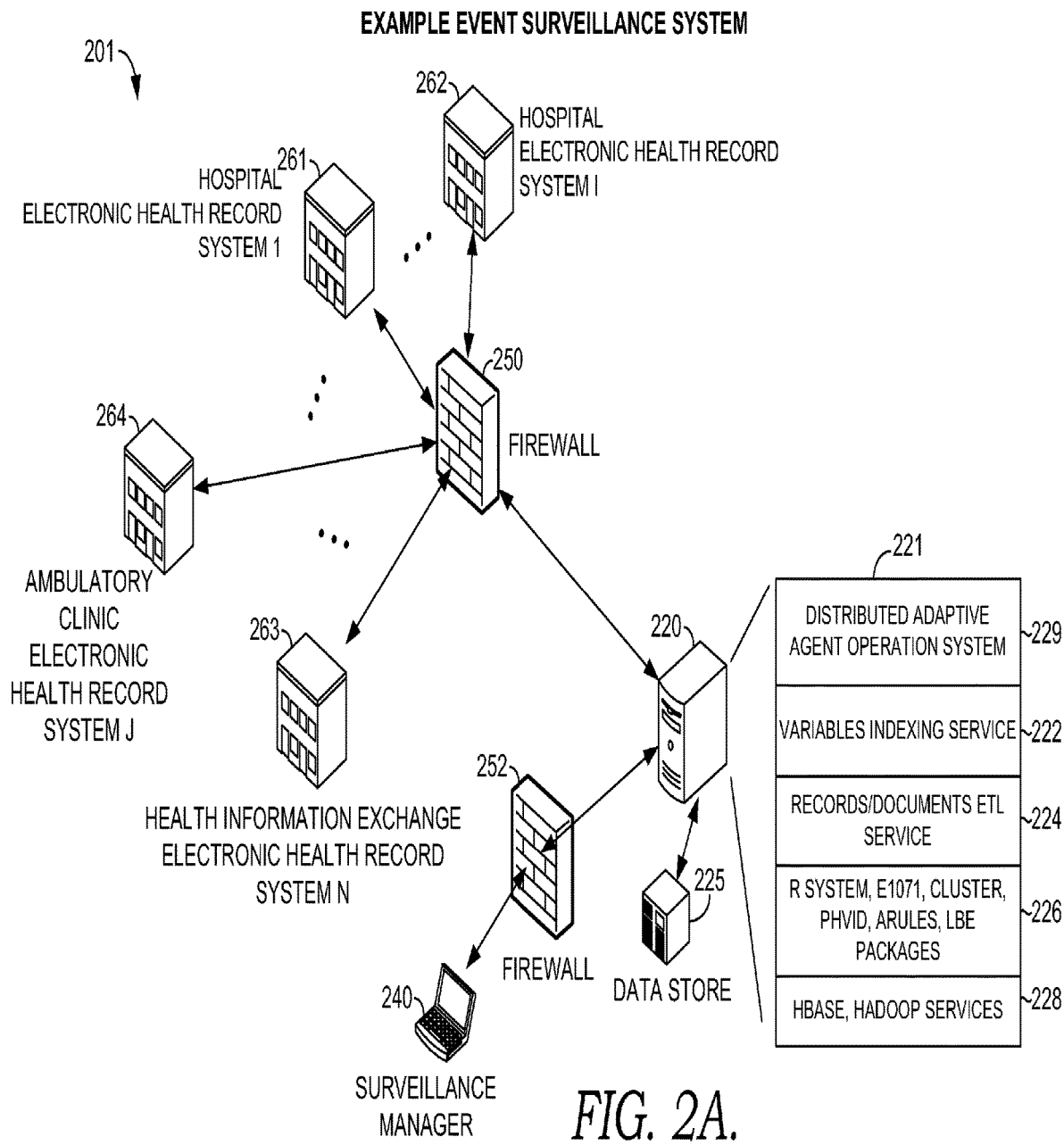
FIGS. 2A, 2B, and 2C depict aspects of an illustrative operating environment suitable for practicing embodiments of the invention.
Figure 2B:
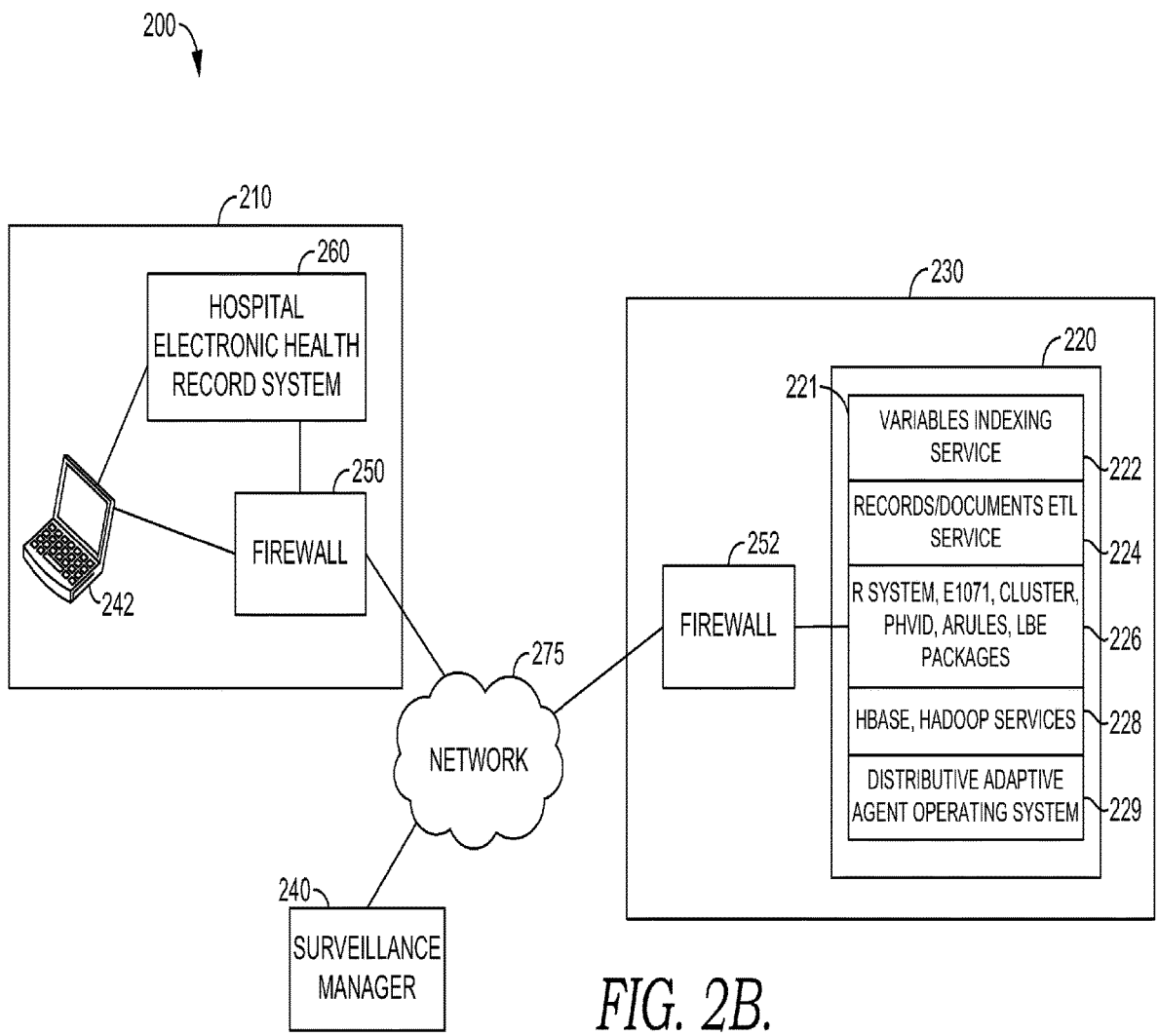

Turning now to FIGS. 2A and 2B, there is presented example operating environments suitable for practicing embodiments of an event surveillance system (ESS). With reference to FIG. 2A, example operating environment 201 includes a computerized system for compiling and running an embodiment of the ESS. In this example operating environment, one or more health record systems such as, for example, Hospital Electronic Health Record System 261, Hospital Electronic Health Record System 262, Ambulatory Clinic Electronic Health Record System 264, and Health Information Exchange Electronic Health Record System 263, are communicatively coupled to a network behind firewall 250, which is communicatively coupled to computer system 220. In embodiments, components of 201 are communicatively coupled over a local or distributed network (not shown) such as the Internet, a public network, or a private network. Embodiments of electronic health record (EHR) systems 261, 262, 263, and 264 include one or more data stores of health records and may further include one or more computers or servers that facilitate the storing and retrieval of the health records. Firewall 250 may comprise a separate firewall associated with each EHR system, in some embodiments. Furthermore, in some embodiments, one or more EHR systems may be located in the cloud or may be stored in data stores that are distributed across multiple physical locations. In some embodiments, examples of EHR systems further include record systems which store real-time or near real-time patient information, such as wearable, bedside, or in-home patient monitors, for example.

Continuing example operating environment 201 further includes computer system 220, which may take the form of a server, which is communicatively coupled through firewall 250 to EHR systems 261, 262, 263 and 264, and also through firewall 252 to surveillance manager 240. In embodiments, surveillance manager 240 may take the form of a software application operating on one or more mobile computing devices, tablets, smart-phones, front-end terminals in communication with back-end computing systems terminals, laptops or other computing devices. In some embodiments surveillance manager 240 includes a Web-based application or collection of applications that is usable to manage services provided by embodiments of the invention.

Embodiments of computer system 220 include computer software stack 221, which in some embodiments can operate in the cloud, as a distributed system on a virtualization layer within computer system 220. Some embodiments of software stack 221 include a distributed adaptive agent operating system 229, which is capable of hosting a number of services such as 222, 224, 226, and 228. Embodiments of services 222, 224, 226 and 228 can run as a local or distributed stack on a collection of personal computers and servers such as 220 and/or a computing device running manager 240. In one embodiment, manager 240 operates in conjunction with software stack 221.

In embodiments, variables indexing service 222 and Records/Documents ETL service 224 provide services that facilitate retrieving frequent item sets, extracting database records, and cleaning the values of variables in records. These services may invoke software services 226 such as the arules software package of the R-project, titled Mining Association Rules and Frequent Itemsets, version 1.0-10. Software packages 226 perform statistical software operations, and include statistical calculation packages such as, in one embodiment, the R system (i.e., the R-project for Statistical Computing, which supports packages or modules of software functions tailored for specific statistical operations, sometimes called R-packages, and which is accessible through the Comprehensive R Archive Network (CRAN) at http://cran.r-project.org); R-system modules or packages including rms (regression modeling strategies), e1701, arules, cluster, PhViD, which is an R package for Pharmaco Vigilance signal Detection that includes functions for computing Bayesian Conditional Probability Neural Network (BCPNN) values, and the BioConductor module LBE. Module LBE provides a procedure for false-discovery rate (FDR) control, or more specifically, for estimating the proportion of true null hypotheses, the false discovery rate (and so the q-values) in the framework of estimating procedures based on the marginal distribution of the p-values without assumption for the alternative hypothesis. Software packages 226 are associated with services 228, which include Apache Hadoop and Hbase framework, or similar frameworks operable for providing a distributed file system.

Example operating environment 201 also includes data store 225, which in some embodiments includes patient data and information for multiple patients; variables associated with patient recommendations; recommendation knowledge base; recommendation rules; recommendations; recommendation update statistics; an operational data store, which stores events; frequent itemsets (such as "X often happens with Y," for example) and itemsets index information; association rulebases, agent libraries, and other information, patient-derived data, health care provider information, for example. Although depicted as a single data store, data store 225 may comprise one or more data stores, or may be in the cloud.

FIG. 2B illustratively depicts another aspect of an example operating environment, referred to herein as 200. Within 200, a first premise location 210 includes a network behind firewall 250 communicatively coupled to network 275. In some embodiments, network 275 includes the Internet, a public network, or a private network. Premise location 210, which may comprise multiple separate geographical locations, further includes EHR system 260, which may comprise multiple separate EHR systems communicatively coupled through a network, as depicted in FIG. 2A. In some embodiments, premise location 210 further includes client computer 242, which communicates with EHR system 260. Example environment 200 further includes a premise location 230 which includes computer system 220 communicatively coupled through firewall 252 to network 275. Additional numbered components of environment 200 in FIG. 2B are described in connection to FIG. 2A.

Figure 2C:
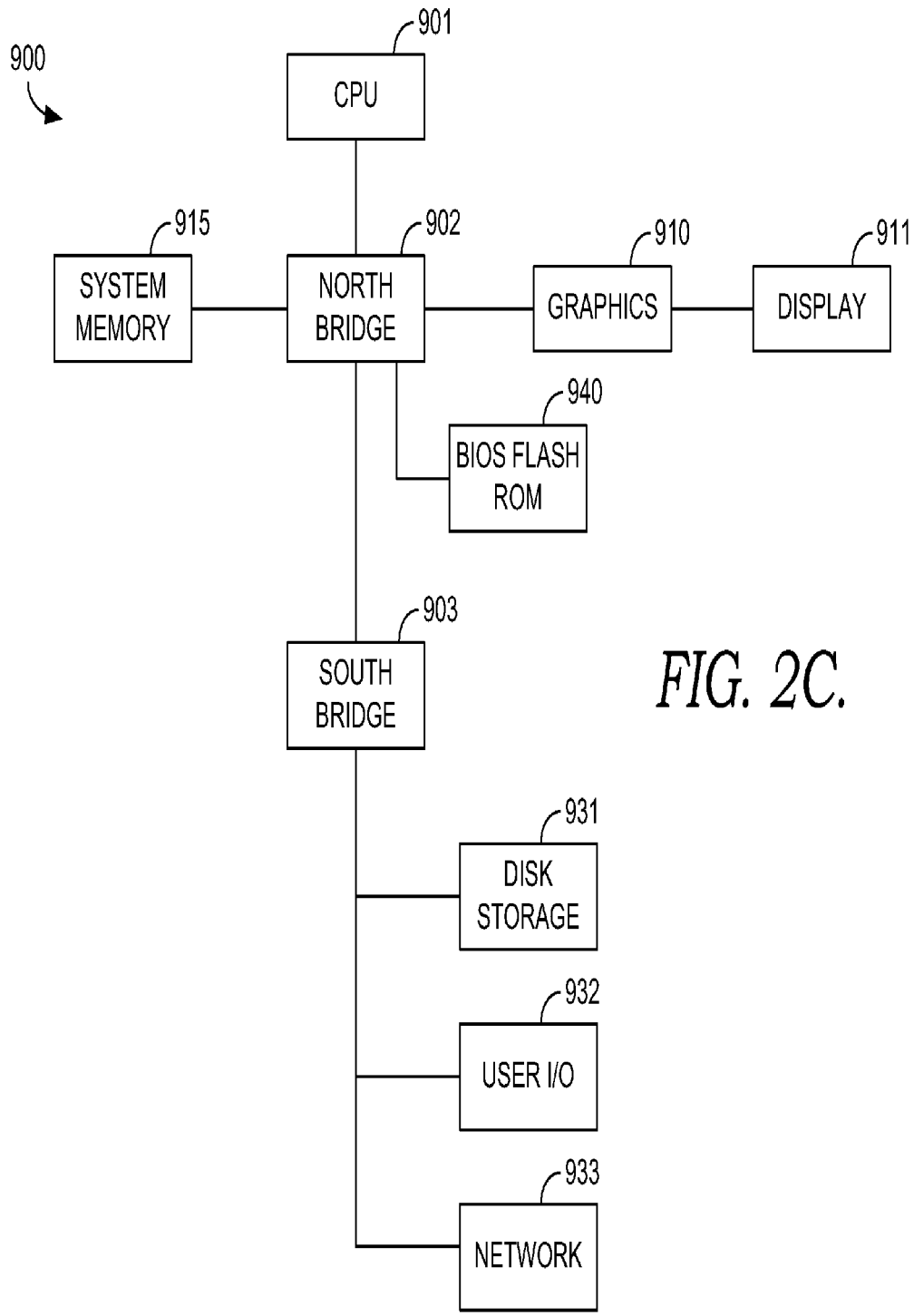

Turning now to FIG. 2C, there is shown one example of an embodiment of computer system 900 that has software instructions for storage of data and programs in computer-readable media. Computer system 900 is representative of a system architecture that is suitable for computer systems such as computer system 220 of FIGS. 2A and 2B, and the computer device(s) operating surveillance manager 240, in some embodiments. One or more CPUs such as 901, have internal memory for storage and couple to the north bridge device 902, allowing CPU 901 to store instructions and data elements in system memory 915, or memory associated with graphics card 910 which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU through south bridge 903 as well. The system architecture depicted in FIG. 2C is merely one example of any number of computer architectures suitable for supporting computer system 220 of FIGS. 2A and 2B.

In some embodiments, computing system 900 is a computing system made up of one or more computing devices. In an embodiment, computing system 900 includes an adaptive multi-agent operating system, but it will be appreciated that computing system 900 may also take the form of an adaptive single agent system or a non-agent system. Computing system 900 may be a distributed computing system, a data processing system, a centralized computing system, a single computer such as a desktop or laptop computer or a networked computing system.

In some embodiments, computing system 900 is a multi-agent computer system with software agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 3:
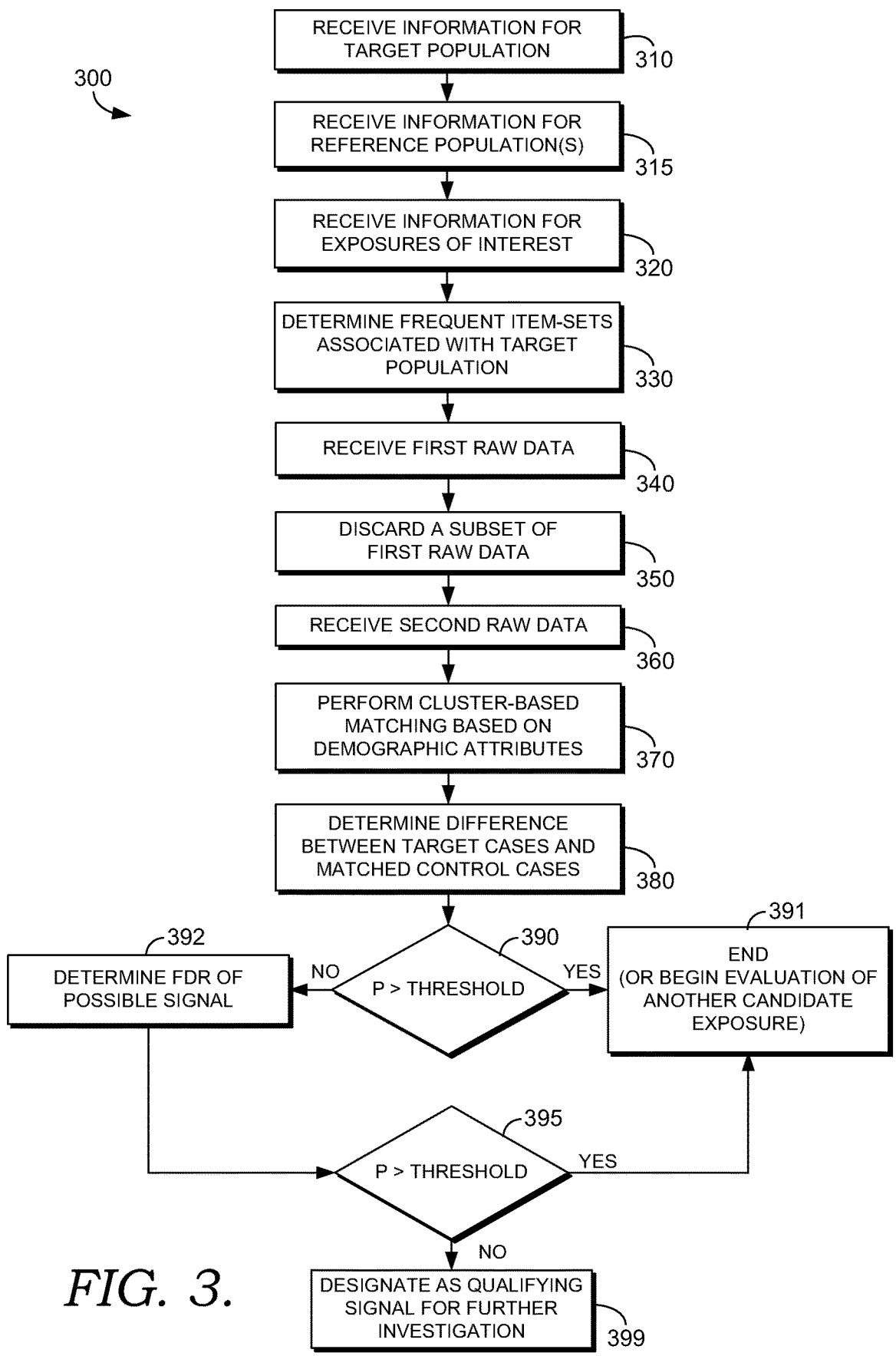
FIG. 3 depicts a flow diagram of a method for generating a synonymy classifier and verifying and validating whether such a classifier achieves statistical sensitivity and specificity in the range of deployment, sufficient for satisfactory performance in the use for detecting and ascertaining safety signals in observational data warehouses comprised of records derived from electronic medical records (EMR) systems, in accordance with embodiments of the invention.

Referring to FIG. 3, a flow diagram is provided which illustrates an embodiment of a system and method for generating a synonymy classifier and verifying and validating whether such a classifier achieves statistical sensitivity and specificity in the range of deployment, sufficient for satisfactory performance in the use for detecting and ascertaining safety signals in observational data warehouses comprised of records derived from electronic medical records (EMR) systems, herein referred to generally as 300.

At a step 310, a first set of health care information about a target population of interest is identified and received. At a step 315, a second set of health care information about a reference population of interest is identified and received. In some embodiments a computer system 220 receives the sets of information from one or more EHR systems such as 260, 261, 262, 263, and/or 264, or from network storage such as data store 225, which may comprise one or more EHR systems, in some embodiments. In some embodiments a user or software agent selects the target and reference populations of interest by establishing attributes and/or inclusion-exclusion criteria and venues that define that population. At step 320 the exposures of interest, including therapeutics exposures that are incident upon members of the population, are identified and received. In some embodiments, exposures of interest include a drug, ingested food, or liquid; product; an environment or an event incident upon a patient, or combination of these. For example, in a target patient population comprising 35- to 60-year-old heart attack patients having an in-patient length of stay greater than 72 hours, an exposure of interest might comprise those patients who were prescribed Ciprofloxacin. In some embodiments, exposures of interest are selected by a user or software agents or recommended by computer system 220. In some embodiments, exposures of interest are received from a recommendation provided by a software agent and/or computer system 220; from software-logic rules such as, for example, the top 500 drugs prescribed most often over a period of time; or inputted by way of a user selection or query.

At a step 330, frequent item-sets associated with the population are determined. In some embodiments, method 300 retrieves frequent item-sets that are statistically associated with the population, including exposures and outcomes events (such as procedures, or statuses, or laboratory results, or clinical exam findings, or diagnoses, for example), with provision for longitudinal record linkage for outcomes that tend to materialize after a latency period has elapsed. In some embodiments, step 330 includes step 320, and in some embodiments, computer system 220 and/or software agents identify exposures of interest by determining frequent item-sets associated with the target population.

In some embodiments, EHR systems or data store 225 are queried for information used to identify frequent item-sets. In some embodiments, one or more software agents, operating as part of a multi-agent computer system 220, facilitate identifying and retrieving frequent item-sets, and in some embodiments, the arules open-source software package of the R-system (or R-project), which is depicted as part of services 226 of FIGS. 2A and 2B, is employed. In some embodiments, a solver agent applies the arules package, and in some embodiments a plurality of software agents may be used, operating in parallel, for determining frequent item-sets from the set of information.

At a step 340, a portion of raw data of the target population identified in step 310, herein referred to as the first raw data, is received. In some embodiments, the first raw data is selected or extracted from the information about the target population, and comprises samples of EHR database records that accrued during a surveillance time period. In embodiments, a first portion of raw data is identified and received from the target population for processing by the present method. Embodiments select the exposures of interest identified at 320 in addition to ancillary demographic data associated with identified data items for each instance of care. Examples of demographic data include the patient type, reason for admission, patient height, patient weight, patient age, patient race, patient sex, units, item description, item notes, reason for care, venue type: home, clinic, emergency, outpatient, surgery, or similar data associated with the patient. In some embodiments data is selected by forming an SQL query over available records identifying necessary data, and restricting records that are within certain ranges of demographic data so as to make the selected data homogeneous. Embodiments restrict the sex, weight, patient age, or care context so as to restrict the chosen records to a certain, chosen, homogeneous demographic subset.

At a step 350, a subset of the first raw data is discarded. In some embodiments, exposure-event combinations that do not have any occurrences or have fewer than a "Q" counts during a period of surveillance are censored. Moreover, in some embodiments the value of Q counts varies according to the event-exposure combination. For example, in the embodiments described in connection to FIGS. 4A and B and FIG. 5, event exposure combinations having fewer than three occurrences (Q=3) during a period being analyzed are removed from the raw data. However, the value of Q may vary to accommodate different sensitivities, rationalized by different use-cases, occurrence ascertainment methods, and value gained/lost by occurrences. Specifically, increasing the Q value would tend to reduce the statistical sensitivity to detect true-positive signals, in principle. The minimum count Q that may be considered actionable may vary according to the event-type, according to the reliability of the method(s) used to ascertain the occurrence or non-occurrence of that event-type, and according to the value associated with the occurrence of the safety event (for example, a reversible event; irreversible event; death of a child who was otherwise well; death of a healthy adult with many dependents; death of an elderly person; death of someone so sick that their survival was improbable no matter what therapeutic regimen might be tried; or similar events).

At a step 360, a portion of raw data of the one or more reference populations identified in step 315, herein referred to as the second raw data, is received. Embodiments identify records from the one or more reference populations that meet the same demographic restrictions that were applied in the selection of the raw data at 340. For example, if the target population is heart attack patients having an in-patient stay of greater than 72 hours, with demographic attributes that identify males, ages 35 to 70, then a subset of information, which comprises the second raw data, is selected or extracted from the one or more reference populations to be restricted to similar demographic attributes, in order to provide a better statistical sample for comparison.

In some embodiments, the data records' variables values received at step 340 and 360 are first "cleaned" or otherwise prepared for processing by services 222 and 224 of FIGS. 2A and 2B. For example, some embodiments clean the data for uniformity, and some embodiments transform data values to a new interval for comparison, and discard data that does not meet quality standards. For example, if a numerical field has a textual entry, this data is discarded, or converted to a numerical value, or if data is in various units, the data is converted to standard units for comparison purposes. Additional examples of discarding data include discarding extreme values from raw data, e.g. default values or obviously erroneous values.

At a step 370, perform cluster-based matching of the reference instances (i.e., information from the reference populations comprising patients who did not have the candidate exposure-event of interest, which serves as a control), to target instances (i.e. information from the target population who receive the candidate exposure). In embodiments, the cluster-based matching is based on the demographic attributes, and is applied to the first raw data from the subset of second raw data to determine one or more clusters. Embodiments apply a cluster method to reduce the dimensionality of the raw data. Some embodiments of applying a cluster method generate a decision-tree classifier. For example, a representative clustering method identifies a first cluster of numeric data and a second cluster of alphabetic data. Another representative clustering method breaks down the data values of a field to be analyzed into a spectrum of numerical values and identifies clumps of values that are relatively close to one another. An exemplary clustering method identifies clusters based on demographic attributes, e.g. breaking down by gender, race, units, description content, notes content, etc.

In some embodiments, the open-source module e1017, a software package in the R-system of services 226 in FIGS. 2A and 2B, is employed to facilitate one-to-one matching against the demographic attributes. For example, for everyone who is a woman, age 37, African-American, has comorbid diabetes with a heart attack, find another patient from the unexposed (reference) population in the cohort that also has these attributes. In embodiments e1071, or similar software services, have the functionality to account for slight variations in the matching attributes, and such variation can be adjusted by the user, in some embodiments. For example, a 36-year-old (instead of 37 year old) woman having the same attributes above may be determined as a match. In some embodiments, one or more software agents facilitate the matching processing, and operate in parallel, thereby allowing a large amount of information to be evaluated for matching in a reduced amount of time.

At a step 380, one or more quantitative measures of the degree to which the groups' event rates differ between the first data of the target population and the second data of the reference group(s), for the target 'cases' and the matched 'controls' as determined in step 370. In embodiments, measures of statistical difference are determined by employing the BCPNN algorithm and may be carried out using a software service 226 such as the open-source PhVid package, version 1.0.3 of the R-system. In some embodiments, the BCPNN algorithm is carried out in parallel with one or more of the MGPS, Emperical Bayes (EB) algorithm, and proportional reporting ratio (PRR) algorithms so that results of each of these algorithms may be provided to a user or software agent enabling the user or software to compare the results for sensitivity in detecting the safety signals.

At a step 390, the output measure P determined in step 380 is compared against a first threshold value to determine whether a statistically significant safety signal exists for the candidate exposure of interest. For example, in embodiments, a comparison is performed, such as PRR>2; BCPNN probability <0.05; or MGPS probability <0.05, wherein a threshold value (e.g., 2 for PRR and 0.05 for BCPNN and MGPS) is empirically established as denoting statistically significant safety signals. In some embodiments, a software agent determines the threshold value and may update or vary the threshold and additional information about patient populations and exposures becomes available. In other words, if the probability P is greater than the threshold, we can accept the null hypothesis that this drug (or other candidate exposure) is no different from all other drugs or exposures, and we can proceed to a step 391, where we quit or go on to next exposure candidate. However, where the probability P is less than the threshold, then there is possible signal(s) indicating that exposure to the candidate is likely to help or harm the patient's condition, or on the other hand, there could be excessive false alarms affecting the possible signal.

Accordingly, where P is less than the threshold, it is necessary in some embodiments, to assure that the signal(s) detected in step 390 are sufficiently unlikely to be false positives or false alarms. Thus, at a step 392 a false discovery rate (FDR) is determined. In some embodiments, an FDR is determined using the Benjamini-Hochberg or other methods for computing FDR. In embodiments, FDR sets a threshold for discriminating signals thereby controlling excessive rates of false alarms. By determining whether a signal is a false positive, a drug (or exposure) that would otherwise be removed from the market due to apparent danger, might otherwise remain. One practical consequence is that where such a drug is the only drug available on the market for a treatment, the drug remains on the market and patients may live instead of die.

At a step 395, the FDR-applied signal is compared against a second threshold value. Where the signal is greater than the threshold, there is likely a high number of false alarms, and the method proceeds to step 391. However, if the signal is lower than the second threshold, then the signal at step 399 is designated as a qualifying signal, potentially indicating that the candidate exposure has a bearing on the patient's disposition. In some embodiments, an ideal signal P may be equal to 0.01 or less.

EXAMPLE

An example embodiment of our event surveillance systems and methods comprising an empirical Bayes confidence-propagation neural network (BCPNN), proportional reporting ratio (PRR), and Multi-item Gamma Poisson Shrinker (MGPS) methods and subsystems, has been reduced to practice. In this example embodiment, computer system 220, comprises a server cluster running the Linux operating system, software packages 226 comprises the open-source statistical software package R, the R modules PhViD version 1.0.3, e1071, cluster, and arules, and the open-source BioConductor module LBE. Retrieval of structured discrete items was performed using Cerner's Discern Explorer™ operating on Cerner Millennium™ systems, one of which had been mapped using Cerner's Controlled Medical Terminology (CMT™) universal concept identifier ontology.

Our example embodiment has been validated by implementing it in high-mortality clinical contexts where conventional 'spontaneous adverse reports' are problematic due to sociological reasons of fear of medical malpractice litigation. In the context of in-patient care of acute myocardial infarction ("heart attack"), electronic medical record systems (EMRs) capture and store all of the transactions related to medication orders and meds administration and also automatically capture and store outcome occurrences electronically. Outcomes may include events or statuses that are observed and entered into the EMR by humans, such as patient expiry vs. patient discharge from the facility alive; however, many outcomes are ones such as laboratory test results and blood pressure and cardiac/hemodynamic parameters that are measured and electronically entered automatically, where humans do not enter but merely review the accumulating information.

With contemporary data warehouse computer systems comprised of EMR information, it is possible to automatically and continually perform data mining of all of the billions of transactions and events and statuses, classifying patterns that meet criteria that do constitute reportable adverse events of various types. It is not necessary that any human doctor or nurse or other person who is engaged in a patient's care notice the ADR-qualifying pattern and make the decision to write and file a spontaneous ADR. Indeed, embodiments of the present invention, including this example embodiment, are motivated (a) by the fact that ordinary human behavior leads to the present under-reporting of safety events, such that it is widely believed that less than 1% of adverse events that do occur are ever reported, and (b) by the consequent failure to detect the adverse events. Instead, embodiments of our invention operating as a data mining system connected to data feeds from a plurality of EMR systems detect the patterns and classify event types. This can include multivariable patterns and sequences that would be beyond the usual practical capabilities of humans to notice or that engender "separation of duties" related fragmentation of attention, especially when the prescriptions or interventions or other attributes that comprise the patterns are undertaken by a plurality of caregivers who may not be aware of what each is respectively doing (for example, the infectious disease doctor prescribing antibiotics for the patient may not bother to look at what medications the cardiologist is using for heart rhythm management or what medication the surgeon is using for preventing nausea and vomiting).

In all, it is routine that an acute myocardial infarction (AMI) patient may have 5 to 15 or more medications administered concomitantly. In the context of managing AMI, giving antiplatelet medication, analgesics, a beta-blocker, additional anti-hypertensives (such as an angiotensin converting enzyme (ACE) inhibitor, or an angiotensin receptor blocker (ARB), or a calcium channel blocker), a medication to help the patient sleep, a proton pump inhibitor (PPI) to prevent stomach ulceration, and an antiemetic are part of current best-practice standard of care. Chronic medications that treat pre-existing conditions that the patient has (such as diabetes, hypercholesterolemia, depression or other mental/behavioral conditions, epilepsy, etc.) are usually sustained throughout the hospital admission. Additionally, if the patient receives angioplasty/stenting (PCI) or coronary artery bypass grafting (CABG) surgery, perioperative antibiotics are prescribed; or, if post-operative infection supervenes, as is quite commonly the case, other antibiotics are used. If hypoperfusion or shock supervenes, still other medications (pressors, inotropes, loop diuretics, etc.) are added. And if abnormal heart rhythms develop, then antiarrhythmic medications are added.

Antiarrhythmic drugs that block the hERG receptor or potassium channel prolong the electrocardiogram QT interval and increase the risk for torsades de pointes, ventricular asystole, and cardiac death. Such drugs include amiodarone, dronedarone, sotalol, quinidine, procainamide, ibutilide, dofetilide, and disopyramide. Additionally, some macrolide and fluoroquinolone antibiotics, phenothiazine antipsychotics/antiemetics and SSRI antidepressants, serotonin agonists of the triptan class, cisapride, antiemetic 5-HT(3) inhibitors such as dolasetron and others have all been reported to also be associated with QT prolongation and cardiac arrhythmias.

Among these, the high likelihood of serious proarrhythmic effects of quinolone antibiotics has long been noted. Ciprofloxacin may be given to select patients because the agent is believed to be safer than levofloxacin, moxifloxacin, or other fluoroquinolone antibiotics, but such a belief is, to date, anecdotal and is not well-founded on evidence. Prolongation of the QT interval related to the effect of fluoroquinolones on rapid potassium channels (IKr) may lead to torsades de pointes and cardiac arrest (ventricular asystole).

Many cases of unexplained cardiac arrest temporally related to fluoroquinolone administration have appeared in the literature. Nonetheless, fluoroquinolones continue to be routinely utilized in acute care contexts where cardiac risk is already elevated, such as populations who are experiencing acute coronary syndrome (ACS) or AMI and are admitted to hospital for treatment. In the percutaneous coronary intervention (PCI) angioplasty/stenting and the coronary artery bypass grafting (CABG) subpopulation, these antibiotics continue to be commonly prescribed in care of such patients, even though there are alternative antibiotics that do not carry such risk of arrhythmias. Furthermore, antibiotics with QT-prolonging side-effects are frequently prescribed in combination with amiodarone, ondansetron, SSRIs, antiepileptics, analgesics, and other medications that compound the risk of cardiac arrest.

Typically, a percentage of patients who are administered fluoroquinolone antibiotics develop marked QTc prolongation (QTc>550 msec) within 24 hours of antibiotic administration. Patients in whom such LQT syndrome develops may have genomic variants in one or more of the pathways involved in metabolizing and excreting the antibiotic or, in other instances, may be on one or more other concomitant medications that are either substrates or inhibitors of enzymes in those pathways, or, in yet other instances, may have comorbid organ system impairments that reduce the physiologic reserve that the organ systems possess to sustainably accommodate the incremental stresses that are placed upon them. Such drug-induced LQT patients tend to experience recurrent syncope, torsades de pointes requiring defibrillation, and other life-threatening hemodynamic and electrophysiologic abnormalities.

FIGS. 4A and 4B each show outcomes, provided in tables 400 and 450, respectively, of example applications of the example embodiment described above. In both example applications of the embodiment, herein referred to as Event Vigilence example A and Event Vigilence example B, data were extracted from a HIPAA-waivered, deidentified data warehouse, called Health Facts®, which receives EMR data feeds on a nightly basis and contains a 100% sample of all episodes of care incident upon 131 U.S. acute care facilities. For the period 1 Jan. 2008 through 31 Dec. 2010, an extraction produced a cohort of 6,699 patients admitted to hospital with AMI that was proven by troponin or creatine kinase MB tests and by electrocardiogram criteria who were between the ages of 35 and 60 years old; who survived at least 72 hours from the arrival at hospital; who had prior episodes of care with one or more measurements of LFTs had been performed wherein the LFT results had been in the normal range (less than the upper limit of normal ULN); and who received one or more measurements of LFTs during the index AMI admission. In this cohort there were 380 in-hospital deaths (5.7%) and 192 instances of LFT-ascertained Grade 4 liver injuries that materialized subsequent to drug exposure (2.9%).

Table 400 of FIG. 4A shows the results of the example embodiment's detection of statistical combinations of exposures (in this example, a drug or combinations of drugs) that were associated with increased relative risk of in-hospital patient death. Table 450 of FIG. 4B shows the results of the example embodiment's detection of statistically significant combinations of exposures (again in this example, a drug or combinations of drugs) that were associated with increased relative risk of developing in-hospital, life-threatening Grade-4 drug-associated liver injury. Ascertainment of the liver injury events was based on laboratory liver function test (LFT) results showing post-exposure increases (alanine aminotransferase ALT>20×ULN; or aspartate aminotransferase AST>20×ULN; or alkaline phosphatase ALKP>20× ULN; or total bilirubin TBIL>10×ULN) over pre-admission baseline values for the LFTs. Each row of tables 400 and 450, correspond to the results of an exposure. For example, row 401 provides results of patients who received Ciprofloxacin; row 402 shows the exposure combination of Amiodarone and Phenytoin, perhaps received by a patient having arrhythmia who also has epilepsy; row 455 shows the exposure combination of Ibuprofen and Levofloxacin. Rows 403 and 453 show the results of the entire cohort (in this example, the cohort, described above, of 6,699 patients admitted to hospital with AMI). Rows 403 and 453 thus provide a baseline mortality. For example, as shown in row 403, 380 patients of the 6,699 cohort (or 5.7%) died, and in row 453, 192 patients sustained irreversible Grade-4 liver injury. More specifically, in each instance, the 380 deaths and 192 incidents of injury are the numbers of patients among a total population of 6,699 AMI inpatients (ICD-9-CM 410.xx) admitted between 1 Jan. 2008 and 31 Dec. 2010 in 131 Cerner Health Facts® contributor institutions, subset of patients who (a) remained alive for length of stay >72 hours, (b) who had one or more ALT, AST, ALKP, and/or TBIL measurements subsequent to the time when the index medication was dispensed, and (c) had one or more values for each of ALT, AST, ALKP, and TBIL in the normal range during episodes of care prior to the index AMI admission. The total 6,699 serves as reference for calculation of relative risk (RR).

Columns 405 and 455 indicate the particular candidate exposure, such as the drug or combination of drugs, being evaluated against the cohort. Columns 410 and 460 show the number of patients who received the exposure; for example, in column 410 of table 400, 386 patients (or 5.8% of the 6,699 cohort) received Ciprofloxacin. Columns 415 and 465 show the actual number of patients, out of the 6,699 cohort, who died (415) or sustained Grade-4 liver injury (465). Columns 420 and 470 show the expected number of patients, out of the 6,699 cohort, who died (420) or sustained Grade-4 liver injury (470). Columns 425 and 475 show a relative risk or likelihood of dying, where the overall population (the cohort of 6,699 patients) is given a value of 1.0. For example, if a particular patient in this cohort would otherwise have a 5.7% chance of dying, and now that patient is given Ciprofloxacin (row 401), then that patient's risk of dying goes up to 33.4% or 5.9 times more likely to die. Thus, while the expected number of deaths (column 420) is only 28.3, the example embodiment shows that the actual number of deaths (column 415) is 129. A surgeon or cardiologist might otherwise prescribe Ciprofloxacin as a peri-operative to prevent infection, unaware of the risk to the patient or that the patient dies several days later.

Continuing with FIGS. 4A and 4B, columns 430 and 480 show the ratio of actual vs. expected number of deaths or sustained Grade-4 liver injuries. Columns 435 and 485 show the determined P-value, such as the P-value described above in connection to method 300 of FIG. 3. In this example embodiment, a Bayesian confidence propagation neural network (BCPNN) algorithm, Empirical Bayes (EB) algorithm, and Gamma Poisson Shrinker algorithm were used for signal detection and p-value calculation. The top 200 medications were extracted from Health Facts® data warehouse. Medications or combinations of concomitant medications with fewer than ten patient exposures to the combo were omitted from the analysis. Medications or combinations of concomitant medications with fewer than three events were omitted from the analysis. A Monte Carlo simulation burn-in comprising 2,000 iterations, followed by 50,000 iterations was applied to produce the expected number counts (columns 420 and 470) and p-values (columns 435 and 485). Columns 440 and 490 show the 'number-needed-to-harm' or NNH, as described above, for each exposure of interest.

Our example event surveillance system and method embodiment discovered 14 exposures (FIG. 4A) that were associated with statistically significant (p<0.05) increased risk of in-hospital mortality, elevated up to 5.9-fold above the mortality risk experienced by the cohort as a whole. It discovered six exposures (FIG. 4B) that were associated with up to 5.3-fold increased risk of Grade-4 liver injury while the patients were in-hospital.

All of the medications in this example are drugs that have been on the market for a relatively long time, so it was possible to validate the signals detected in the 2008-2010 inpatient AMI cohort by comparing to data extracted for the 7,103-patient inpatient AMI cohort from the de-identified EMR-derived records incident upon the same institutions participating in the Cerner Health Facts® data warehouse during the period 1 Jan. 2005 through 31 Dec. 2007. The same signals were identified in the 2005-2007 cohort, at approximately the same p-value significance levels. This example scenario reveals that there are several clinically-important and heretofore-unrecognized exposures of AMI patients to individual medications and combinations of medications that are unsafe, in terms of significantly increased risk of mortality and/or life-threatening drug-associated liver injury.

This finding is important not only with regard to the fact that none of the manufacturers of the drugs involved, nor the national regulatory agencies, have previously identified these safety signals in human-submitted spontaneous adverse drug reaction (ADR) reports, and therefore have evidently failed to prevent injury and death because of false-negative errors and inability to detect such signals in the sparse spontaneous ADR submissions. The finding is also important insofar as it illustrates (a) the profound improbability of conventional prior art systems and of current practices implemented by regulators and manufacturers, to detect important patterns that involve second- or higher-order combinations of exposures that are outside the purview and responsibility of any one manufacturer or any one therapeutic product, and (b) the previously under-appreciated way in which relatively common comorbid conditions confer disproportionate risks on certain subsets of the population (e.g., people who develop a sequelae or complications (for example, arrhythmias) secondary to or comorbid with the index context (for example, AMI); people with epilepsy who are on anticonvulsant medications; people with depression or psychosis who are on antidepressant or antipsychotic medications). The example reveals that one serious acute condition, such as AMI, can create a clinical and pharmacotoxicologic context wherein a drug that is ordinarily safe and effective in a healthier population in which the drug is labeled for use can become unsafe to use, at least in the routinely prescribed forms and dosages. The example highlights how prior art and conventional systems and methods that entail diluted, aggregated populations pooling a predominant percentage of people who do not have that condition with a modest percentage of people who do have the condition, can result in failure to detect a signal (false-negative Type II statistical error). Further, it reveals how components of routine standing-orders and order-sets and protocols (e.g., NSAID analgesics; perioperative antibiotics; 5-HT(3) inhibitor or phenothiazine antiemetics) that are conventionally regarded as very safe and, thus, are prescribed in a de rigeur, uncritical fashion can, given the right context and concomitant second- or higher-order combinations of factors, become distinctly unsafe in-context, in a manner that doctors, regulators, and manufacturers would all have difficulty detecting without the assistance of embodiments of the invention.

Figure 5B:
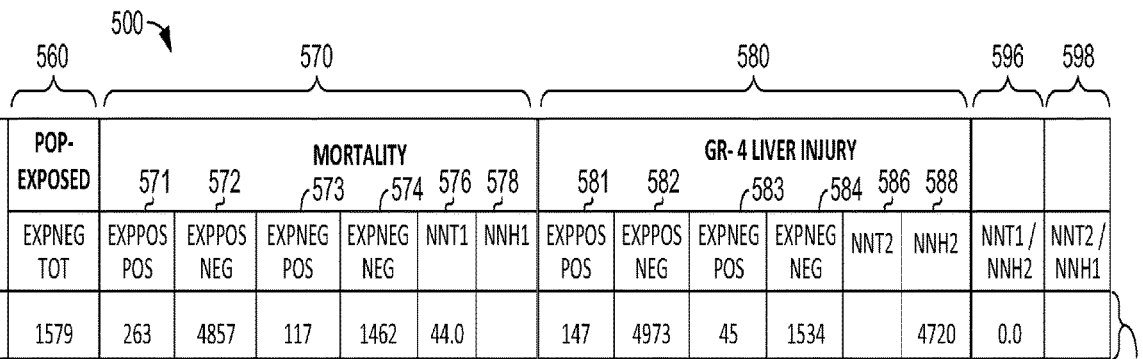

Turning now to FIGS. 5A and 5B, a portion of results from the application of the actual reduction to practice of the embodiment described above in connection to FIGS. 4A and 4B, is provided in table 500, which is shown across FIGS. 5A and 5B. In table 500, each row, such as row 501 shows information of an exposure of interest (column 505), such as a drug or combination of drugs. As described above, this example application uses a cohort of 6,699 AMI inpatients admitted between 1 Jan. 2008 and 31 Dec. 2010 in 131 Cerner Health Facts® contributor institutions, who (a) remained alive for length of stay >72 hours, (b) who had one or more ALT, AST, ALKP, and/or TBIL measurements subsequent to the time when the index medication was dispensed, and (c) had one or more values for each of ALT, AST, ALKP, and TBIL in the normal range during episodes of care prior to the index AMI admission. Column 510 shows the number of patients who received the exposure of interest (column 505). Column 515 shows the exposure prevalence or percentage of the total 6,699 population who were exposed to the drug or drug combination; thus, for example, 76.4% (or 5120) of the 6,699 patients received acetaminophen, suggesting that prescribing acetaminophen is a common procedure for patients belonging to the reference population (i.e. the 6,699 patients of the cohort). Columns 520, 525, 530, 535, and 540 show the count of adverse events resulting from the exposure. Here, AE1 of column 520 shows in-house morality, as a count and also as a percentage of the count from the number receiving exposure (column 510); AE2-AE5 (columns 525, 530, 535, and 540, respectively) show the count for grade 1-4 liver injuries. Column 545 shows the percentage of Grade-4 liver-injury count (column 540) from the number receiving exposure (column 510).

Example results indicating likely qualifying signals can be observed in items 521 and 523, in column 520, of Table 500. Items 521 and 523 are specific values of in-house mortality parentages, where 521 shows higher percentages (8.6%, 10.1%, and 13.5%) than the 5.7% of the cohort that died, while 523 shows a lower percentage 3.4%, indicating here that patients of this cohort may be less likely to die when exposed to atorvastatin.

Continuing with table 500, in FIG. 5B, column 560 shows the total negative exposed count (i.e. the total population of the cohort (6,699) minus the number receiving exposure (column 510)). The columns of 570 and 580 represent metrics associated with mortality and Grade-4 liver injury, respectively. Columns 571 and 581 show the count of patients who received exposure to the drug or exposure of interest who died (column 520) or sustained grade-4 liver injury (column 540). Columns 572 and 582 show the count of patients who were exposed to the drug (or exposure of interest) who did not die (i.e. column 572 equals column 510 minus column 571) or sustain Grade-4 liver injury (i.e. column 582 equals column 510 minus column 581). Columns 573 and 583 show the count of patients who were not exposed to the drug (or exposure of interest) and who died (column 573 equals the total number of patients in the cohort who died (380) minus column 571) or sustained Grade-4 liver injury (column 583 equals the total number of patients in the cohort who sustained Grade-4 liver injury (192) minus column 581). Columns 574 and 584 show the count of patients who were not exposed to the drug (or exposure of interest) and who did not die (column 574 equals column 560 minus column 573) or did not sustain Grade-4 liver injury (column 584 equals column 560 minus column 583). Finally, columns 576 and 586 show NNT1 for mortality and NNT2 for Grade-4 liver injury, respectively, and columns 578 and 588 show NNH1 for mortality and NNH2 for Grade-4 liver injury, respectively. In this example NNT1 can be determined as: 1/([column 510]−[column 571]/[column 510]−([column 560]−[column) 573])/[column 560]), where NNT1 is not less than zero. NNT2 of column 586 can be determined similarly using columns 581 and 583 in place of 571 and 573, respectively.

NNH1 can be determined as: 1/([column 571]/[column 510]−[column 573]/[column 560]), where NNH1 is not less than zero. NNH2 of column 588 can be determined similarly using columns 581 and 583 in place of 571 and 573, respectively. Finally, columns 596 and 598 provide ratios of NNT to NNH for assessing the balance of probable benefits and harms, as described above.

ADDITIONAL EXAMPLE EMBODIMENTS

Additional example embodiments include: A system, method, and computer readable media are provided for discovering and validating latent relationships in a dataset, including pharmacovigilance data, medical device vigilance data, or therapeutic procedures and services data, comprising: (i) determining a sample size-independent measure of association between two conditions of interest in the dataset of pharmacovigilance data on a suitably programmed computing device; (ii) analyzing a hypergeometric distribution to determine a measure of statistical unexpectedness between the conditions of interest in said dataset on a suitably programmed computing device, wherein said distribution is based on an urn model under a hypothesis that said conditions are statistically independent; and (c) displaying the measure of association with the measure of the statistical unexpectedness to identify, a significant association between the conditions of interest on a suitably programmed computing device, and involving: (a) obtaining or extracting the records and/or documents (corpora) from a plurality of source record-keeping systems or computer databases; (b) selecting the raw data for a plurality of variables, together with demographic and clinical attributes associated with the cases from the episodes of care that were associated with each data item; (c) establishing for any particular candidate group of patients having exposure to a therapeutic (or therapeutic "combo" or "sequence") of interest, one or more corresponding 'reference' or 'comparator' populations whose attributes are statistically well-matched to those of the candidate group; and (d) omitting to include exposure combination-event vectors that have zero counts or, more preferably, that have fewer than 3 counts that have been accessioned during the relevant time period that is the subject of analysis. In some embodiments the measure of association is a relative risk or an odds ratio.

The system, method, and computer readable media described above, wherein the dataset comprises binary data (such as data with values of yes or no, true or false, "1" or "zero", for example) and the measure of association comprises a reporting ratio such as PRR, or BCPNN p-value, or MGPS p-value, or similar measures of relative risk and significance. Furthermore, in some embodiments, the significant association between the conditions of interest is determined if the NNH is small, generally less than 30, or if the balance of likely benefit and harm for the conditions of interest, as reflected by the ratio NNT/NNH, is significantly greater than 1 and the seriousness and probability of likely harm exceeds the magnitude and probability of the likely benefit that can be expected by undertaking the pattern of therapeutic actions. In some embodiments, the significance threshold is adjusted for multiple comparisons, and in some embodiments, the significance threshold is adjusted using an algorithm to estimate the False Discovery Rate (FDR), such as the Benjamini-Hochberg algorithm, wherein the significance threshold is adjusted to θ/M where M represents the number of comparisons between the first and second conditions of interest.

Furthermore, in some embodiments of the system, method, and computer readable media described above, the first condition of interest is a fixed reference condition, and the second condition of interest is at least one relevant comparison condition or population. Still further, in some embodiments, the first condition of interest is a presence of a drug and the second condition of interest is an adverse event.

In some embodiments of the system, method, and computer readable media described above, displaying the measure of association comprises separately indicating negative associations with reporting ratios less than one from positive associations with reporting ratios greater than one, and in some embodiments, displaying the measure of association comprises displaying statistically significant absent conditions in which NAB=0.

In some embodiments of the system, method, and computer readable media described above, the dataset is partitioned into one or more subsets, and steps (a) through (c) are performed on each subset. In some embodiments the step of partitioning the dataset into subsets comprises partitioning into fixed size moving window partitions based on an index of records in the dataset or on one or more fields in the records in the dataset. In some embodiments, these fields in the records comprise one of a reporting date, a gender, or an age. In some embodiments, the step of partitioning the dataset into subsets comprises using a nearest neighbor partitioning which applies a distance function to the one or more fields in the records in the dataset, and in some embodiments, the step of partitioning the dataset comprises using cluster based partitioning. In some embodiments, the corresponding measures of association displayed as points from the corresponding subsets of data are visually linked together using vectors. In some embodiments, the measure of association and the statistical unexpectedness for each subset is plotted on a graph as a trajectory in which the variations across the subsets are indicative of variations in time or dosage. In some embodiments, the subsets indicate data collected over time, and in some embodiments, the measure of association is tracked longitudinally while the measure of statistical unexpectedness may decrease, increase, or remain constant over time.

Some embodiments of the system, method, and computer readable media described above further comprises combining the first and second conditions of interest, when a significant association between the first and second conditions of interest is determined, as a new fixed first condition of interest, and repeating steps (a)-(c) with a third condition of interest represented as a new second condition of interest. Further, in some embodiments, the new first condition of interest is a combination of a drug and an adverse event while the new second condition of interest is another drug. Some embodiments further comprise constructing and plotting the conditions of interest while the partitioning step varies partitions based on selecting different fields and/or values of fields used for partitioning the dataset into subsets.

In some embodiments of the system, method, and computer readable media described above, the step of determining a significant association comprises using likelihood-of-association information from a medical and biological database. Further, in some embodiments, the biological or medical databases comprise information from biological pathways affected by each drug, encoded in the form of a numerical vector.

In some embodiments of the system, method, and computer readable media described above, pairs of a first condition and a second condition include one among a particular drug and a second drug taken with the particular drug, or a first adverse event and a second adverse event that occurs with the first adverse event.

Some embodiments of the system, method, and computer readable media described above further comprise (1) taking a number of samples from the dataset; (2) recalculating the reporting ratio and the measure of unexpectedness for each of the number of samples; and (3) displaying a confidence box around an adverse event based on corresponding points for that adverse event for each of the calculated and recalculated reporting ratios and the measure of unexpectedness for each of the number of samples. Further, in some embodiments, each of the samples contain between 40-80% of the records in the database, and in some embodiments, each of the samples are selected to eliminate records containing a certain percentage of drugs in the dataset.

In some embodiments of the system, method, and computer readable media described above, the measure of association is displayed using color coded values indicative of either the data underlying the particular association or a significance of the association.

Some embodiments of the system, method, and computer readable media described above further comprise (I) taking a number of samples from the dataset; (II) recalculating and displaying as points the reporting ratio and the measure of unexpectedness for each of the number of samples; and (III) displaying points corresponding to the same pair of conditions across the number of samples in an integrated display by a vector.

Additional embodiments include a system comprising a central processing unit and memory containing logic (CPU) for analyzing a dataset of EMR-derived data, comprising: (a) an input data feed for extracting and transferring the dataset of pharmacovigilance data; (b) a processing unit configured to: (i) determining a sample size-independent measure of association between two or more conditions of interest in the dataset of pharmacovigilance data; and (ii) analyzing a the data to determine a measure of statistical unexpectedness between the conditions of interest in said dataset; and (c) a display unit for displaying the measure of association with the measure of the statistical unexpectedness to identify a significant association between the conditions of interest.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more computer-readable storage devices having computer-usable instructions embodied thereon that, when executed by one or more processors, facilitate performing a method for determining an unsafe combination of therapeutic interventions for human patients in a treatment context where therapeutics interventions are administered by a plurality of caregivers, the method comprising:

determining, by means of a software agent, a target population and a reference population, the determining based at least in part on the software agent identifying a plurality of inclusion criteria and a plurality of exclusion criteria that define the target population and the reference population;

extracting a set of target information from, a data store, the target information associated with the target population of patients from a first set of records of a first health-records system;

extracting from the data store, reference information associated with a reference population of patients from a second set of records of a second health-records system within the data store;

computing, by a processor, an exposure of interest comprising administration of a drug to treat a condition;

computing by the processor, frequent item-sets associated with the target population, a frequent item set comprising the exposure of interest and an associated medical event experienced by a patient;

selecting, by the software agent, first raw data from the target information associated with the target population comprising a first plurality of patients associated with the exposure of interest and one or more demographic restrictions;

selecting, by the software agent, second raw data from the reference information associated with the reference population comprising a second plurality of patients that did not receive the drug, but that received one or more concomitant comparator drugs to treat the same condition, and that meet the same demographic restrictions applied in the selection of the first raw data;

computing by the processor, using a Bayesian confidence-propagation neural network or Multi-item Gamma Poisson Shrinker, a cluster-based matching of the first and second raw data to determine one or more clusters, wherein the cluster-based matching is based on a match between one or more demographic attributes of patients in the second raw data who did not receive the drug, and patients in the first raw data who received the drug;

determining, by the processor, at least one quantifying difference in event rates for the associated medical event between the patients in the first raw data and the patients in the second raw data for at least one cluster;

comparing, by the processor, the quantifying difference to a first predetermined threshold to create a provisional association of one or more of the first plurality of patients to the exposure of interest;

generating by the processor, a safety signal corresponding to the provisional association, the safety signal indicating at least a second order combination and sequence of therapeutics associated with adverse events; and transmitting the safety signal to a data store accessible to the plurality of caregivers to limit application of the second order combination and sequence of therapeutics to a subsequent patient by the plurality of caregivers.

2. The computer-readable storage devices of claim 1, further comprising:

determining a false discovery rate of a first measure to determine a second measure; and comparing the second measure to a second predetermined threshold to create a provisional association of one or more of the first plurality of patients to the exposure of interest.

3. The computer-readable storage devices of claim 2, wherein the false discovery rate is determined using a Benjamini-Hochberg algorithm.

4. The computer-readable storage devices of claim 1, wherein the selecting first raw data from the target information comprises selecting records containing demographic attributes associated with episodes of care that are associated with a data item.

5. The computer-readable storage devices of claim 1, wherein the determining at least one measure quantifying difference comprises using a Bayesian Confidence Propagation Neural Network algorithm.

6. The computer-readable storage devices of claim 1, wherein the determining at least one measure quantifying difference comprises using a Bayesian Confidence Propagation Neural Network algorithm and at least one of a proportional reporting ratio algorithm, Empirical Bayes algorithm, and a Multi-item Gamma Poisson Shrinker algorithm.

7. The computer-readable storage devices of claim 6, wherein the at least one measure determined using the Bayesian Confidence Propagation Neural Network algorithm is compared with each measure of the at least one measure determined using the at least one of the proportional reporting ratio algorithm, Empirical Bayes algorithm, and a Multi-item Gamma Poisson Shrinker algorithm.

8. The computer-readable storage devices of claim 1, wherein a therapeutic intervention comprises specific medications or combinations of medications or specific doses or cumulative exposures to a medication or combination; or invasive procedures such as surgeries; or plans of care or treatment protocols and wherein the target information and reference information comprise pharmacovigilance data, medical device vigilance data, or therapeutic procedures and services data.

9. The computer-readable storage devices of claim 1, wherein a combination of therapeutic interventions comprising the exposure of interest includes: three or more specific medications; a combination of two or more medications with specific doses or cumulative exposures to at least one of the two or more medications; invasive procedures; plans of care or treatment protocols; combinations of specific medications or therapies and invasive procedures, plans of care, or treatment protocols; or specific sequences involving medications, therapies, invasive procedures, and or treatment protocols.

10. A computer-implemented method of discovering patient-context sensitive adverse events (AEs) resulting from an exposure of one or more therapeutics to a human patient, said method comprising:

utilizing one or more processing devices:

determining, by means of a software agent, a target population and a reference population, the determining based at least in part on the software agent identifying a plurality of inclusion criteria and a plurality of exclusion criteria that define the target population and the reference population;

extracting a set of target information from, a data store, the target information associated with the target population of patients from a first set of records of a first health-records system;

extracting from the data store, reference information associated with the reference population of patients from a second set of records of a second health-records system within the data store;

extracting from the data store, exposure information specifying an exposure of interest, the exposure comprising administration of a drug to treat a condition;

computing, by means of the processing device, item-sets including frequent item-sets associated with the target population wherein a frequent item set comprises the exposure of interest and an associated medical event experienced by a patient;

selecting by the software agent, first raw data from the target information associated with the target population comprising a first plurality of patients associated with the specified exposure of interest and one or more demographic restrictions;

selecting, by the software agent, second raw data from the reference information associated with the reference population comprising a second plurality of patients that did not receive the drug, but that received one or more concomitant comparator drugs to treat the same condition, and that meet the same demographic restrictions applied in the selection of the first raw data;

computing, by the processing device, a Bayesian confidence-propagation neural network or Multi-item Gamma Poisson Shrinker mark code combinations, a cluster-based matching of the first and second raw data to determine one or more clusters, wherein the cluster-based matching is based on a match between one or more demographic attributes of patients in the second raw data who did not receive the drug, and patients in the first raw data who received the drug;

determining, by the processing device, at least one measure quantifying a difference in event rates for the associated medical event between the patients in the first raw data and the patients in the second raw data for at least one cluster;

comparing, by the processing device, the at least one measure to a first predetermined threshold to create a provisional association of one or more of the first plurality of patients to the exposure of interest;

determining, by the processing device, a safety signal corresponding to the provisional association, the safety signal indicating at least a second order combination and sequence of therapeutics associated with adverse events; and transmitting a record of the safety signal in a data store accessible by the software agent to limit application of the second order combination and sequence of therapeutics to a subsequent patient by the plurality of caregivers.

11. The computer-implemented method of claim 10, further comprising:
determining a false discovery rate of the at least one measure to determine a second measure; and
comparing the second measure to a second predetermined threshold to create a provisional association of one or more of the first plurality of patients to the exposure of interest.

12. The computer-implemented method of claim 10, wherein the selecting first raw data from the target information comprises selecting records containing demographic attributes associated with episodes of care that are associated with a data item.

13. The computer-implemented method of claim 10, wherein the determining at least one measure quantifying difference comprises using a Bayesian Confidence Propagation Neural Network algorithm.

14. The computer-implemented method of claim 10, wherein the determining at least one measure quantifying difference comprises using a Bayesian Confidence Propagation Neural Network algorithm and at least one of a proportional reporting ratio algorithm, Empirical Bayes algorithm, and a Multi-item Gamma Poisson Shrinker algorithm.

15. The computer-implemented method of claim 10, wherein the at least one measure determined using the Bayesian Confidence Propagation Neural Network algorithm is compared with each measure of the at least one determined using the at least one of the proportional reporting ratio algorithm, Empirical Bayes algorithm, and a Multi-item Gamma Poisson Shrinker algorithm.

16. A system for determining an unsafe combination of therapeutic interventions for human patients in a treatment context where therapeutics interventions are administered by a plurality of caregivers, comprising:
one or more data stores that store healthcare information; and
one or more processors that:
determine, by means of a software agent, a target population and a reference population, the determining based at least in part on the software agent identifying a plurality of inclusion criteria and a plurality of exclusion criteria that define the target population and the reference population extract, from the one or more data stores, target information associated with the target population of patients from a first set of records of a first health-records system;

extract receive, from the one or more data stores, reference information associated with a reference population of patients from a second set of records of a second health-records system;

compute, by the processor, an exposure of interest comprising administration of a drug to treat a condition;

compute, by the processor, items sets including frequent item-sets associated with the target population, wherein a frequent item set comprises the exposure of interest and an associated medical event experienced by a patient;

select, by the software agent, first raw data from the target information associated with the target population comprising a first plurality of patients associated with the exposure of interest and one or more demographic restrictions;

select, by the software agent, second raw data from the reference information associated with the reference population comprising a second plurality of patients that did not receive the drug, but that received one or more concomitant comparator drugs to treat the same condition, and that meet the same demographic restrictions applied in the selection of the first raw data;

compute, by the processor, a Bayesian confidence-propagation neural network or Multi-item Gamma Poisson Shrinker mark code combinations, a cluster-based matching of the first and second raw data to determine one or more clusters, wherein the cluster-based matching is based on a match between one or more demographic attributes of patients in the second raw data who did not receive the drug, and patients in the first raw data who received the drug, the at least one measure quantifying difference in event rates quantified using at least a neural network;

determine, by the processor, at least one measure quantifying a difference in event rates for the associated medical event between the patients in the first raw data and the patients in the second raw data for at least one cluster;

compare, by the processor, the quantifying difference to a first predetermined threshold to create a provisional association of one or more of the first plurality of patients to the exposure of interest;

generate, by the processor, a safety signal corresponding to the provisional association; and transmit the safety signal in a data store accessible to the plurality of caregivers to limit application of the combination of therapeutics corresponding to the provisional association to a subsequent patient by the plurality of caregivers.

17. The system of claim 16, further comprising the one or more processors that:
determine a false discovery rate of the at least one measure to determine a second measure; and
compare the second measure to a second predetermined threshold to create a provisional association of one or more of the first plurality of patients to the exposure of interest.

18. The system of claim 17, wherein the false discovery rate is determined using a Benjamini-Hochberg algorithm.

19. The system of claim 16, wherein the selecting first raw data from the target information comprises selecting records containing demographic attributes associated with episodes of care that are associated with a data item.

20. The system of claim 16, wherein the neural network comprises using a Bayesian Confidence Propagation Neural Network algorithm.

\* \* \* \* \*